United States Patent [19]
Bosley et al.

[11] Patent Number: 5,658,769
[45] Date of Patent: Aug. 19, 1997

[54] PROCESS FOR THE ESTERIFICATION OF CARBOXYLIC ACIDS WITH TERTIARY ALCOHOLS USING A LIPASE FROM *CANDIDA ANTARCTICA*

[75] Inventors: John Anthony Bosley, Kettering; John Casey, Wellingborough; Alasdair Robin Macrae, Newton Blossomville; Gary MyCock, Higham Ferrers, all of Great Britain

[73] Assignee: Unichem Chemie BV, Gouda, Netherlands

[21] Appl. No.: 571,925

[22] PCT Filed: Jun. 21, 1994

[86] PCT No.: PCT/EP94/02060

§ 371 Date: Apr. 8, 1996

§ 102(e) Date: Apr. 8, 1996

[87] PCT Pub. No.: WO95/01450

PCT Pub. Date: Jan. 12, 1995

[30] Foreign Application Priority Data

Jul. 2, 1993 [EP] European Pat. Off. .............. 93305204

[51] Int. Cl.$^6$ ........................................................ C12P 7/62
[52] U.S. Cl. ...................... 435/135; 435/134; 435/174; 435/176; 435/177; 435/180; 435/198
[58] Field of Search ................................ 435/135, 134, 435/176, 177, 180, 198, 174

[56] References Cited

FOREIGN PATENT DOCUMENTS 506 159  9/1992  European Pat. Off. .

OTHER PUBLICATIONS

Aleksey Zaks et al: "Enzymatic catalysis in organic media at 100 C", Science, vol. 224, No. 4654, Jun. 15, 1984, pp. 1249–1251, cited in the applications, see abstract, see p. 1250, right column, paragraph 2; see p. 1251, left column, paragraph 2.

Brackenridge, et al: "Enzymatic resolution of oxalate esters of a tertiary alcohol using porcine pancreatic lipase", Journal of the Chemical Society, Perkin Transactions 1, No. 10, May 21, 1993, pp. 1093–1094, see p. 1093, left column, paragraph 1.

Heldt–Hansen et al: "A new immobilized positional non-specific lipase for fat modification and ester synthesis", ACS Symposium Series, Biocatalysis In Agricultural Biotechnology, vol. 389, 1989, pp. 158–172, see abstract, see p. 158, para.1,–p. 159, para 1,–see p. 160, para. 4, –see p. 166, para. 2, –see p. 171, para. 1 –para. 4.

*Primary Examiner*—Jean C. Witz
*Attorney, Agent, or Firm*—Cushman Darby & Cushman IP Group Pillsbury Madison & Sutro LLP

[57] ABSTRACT

Esters in which the alcohol part is sterically hindered around the ester bond, i.e. derived from tertiary alcohols are enzymatically prepared under low water conditions using *Candida antarctica* lipase A or a lipase species having a substrate activity similar to that of *Candida antarctica* lipase A with respect to tertiary alcohol esters.

9 Claims, No Drawings

PROCESS FOR THE ESTERIFICATION OF CARBOXYLIC ACIDS WITH TERTIARY ALCOHOLS USING A LIPASE FROM *CANDIDA ANTARCTICA*

The present invention relates to a process of enzymatically preparing esters of carboxylic acids using a lipase.

It is known, for example from WO-A-8802775 (Novo Industri A/S) to use lipase in ester hydrolysis, ester synthesis and interesterification (acidolysis, alcoholysis, ester interchange) reactions, but all these reactions have been restricted to the use of primary and secondary alcohols.

In French Patent Specification FR-A-2,617,501 (Soc. Nat. Elf Aquitaine) it has even been proposed to carry out enzymatic reactions in tertiary alcohols, like t-butanol, or t-amyl alcohol, as a solvent, thus indicating that no reaction was expected to occur at all between this solvent and the substrate to be treated with the enzyme. This view is confirmed experimentally by S. Okumura et al. in Biochim. Biophys. Acta 575, 156–165 (1979) in which the ester synthesis by microbial lipases was investigated. None of the lipases of *Aspergillus niger, Rhizopus delemar, Geotrichum candidum* or *Penicillum cyclopium* was able to synthesize esters of tertiary alcohols, phenols or sugar alcohols (see especially Table I).

Porcine pancreatic lipase was found by A. Zaks and A. M. Klibanov to catalyse the alcoholysis reaction between tributyrin and various primary and secondary alcohols in a 99% organic medium (Science 224 (15 Jun. 1984) 1249–1251). It was found that dry lipase was completely inactive in the alcoholysis reaction with tertiary alcohols, but in Table I it has been indicated that the initial rate of the alcoholysis reaction between tributyrin and t-butanol catalysed by wet porcine pancreatic lipase (3.6 wt % water in the enzyme) is 22 μmole/h per 100 mg of lipase. There is no indication, however, of any yields of product.

Finally, I. L. Gatfield has described (Lebensm.-Wiss. u.-Technol. 19 (1986) 87–88) the enzymatic synthesis of esters in non-aqueous heterogeneous systems under the influence of the lipase from *Mucor miehei* (ex Rapidase, Seclin, France). It was found that both primary and secondary aliphatic alcohols can be esterified efficiently, but not tertiary alcohols. In Table 1 t-butanol has been indicated to exhibit a degree of esterification with oleic acid (in equimolar quantities of acid and alcohol; using 3 wt % of the *Mucor miehei* enzyme; magnetic stirring in closed vessels at room temperature for 3 days) of 14%. A repetition of this experiment by applicants of the present application did not produce any t-butyl oleate, however, and it is assumed that the measured degree of esterification of 14% in fact relates to impurities (particularly secondary butanol) present in the t-butanol, since the detection technique used was based on titration, which does not differentiate between the individual ester species.

The absence of any acid numbers and ester values in this article does not allow any further conclusions, but in their German Patent Application DE-A-3,108,927 (referred to in the article) the inventors calculate the degree of conversion from the acid numbers and ester values, as is usual in this type of reactions, but although in this patent application also *Mucor miehei* lipase (Esterase 30,000; Trade Mark, ex Rapidase, Seclin, France) is used, the invention is clearly restricted to primary and secondary alcohols, which clearly speaks for the non-reactivity of the tertiary alcohols in this enzymatic reaction.

In the enzymatic ester synthesis from alcohols and acids it has up till now therefore thought to be impossible to synthesize esters in which the alcohol part is sterically hindered around the ester bond, i.e. esters derived from tertiary alcohols. The availability of such an enzymatic ester synthesis would be of value, however, particularly in the synthesis of "chemically clean" esters, in which no traces of any catalysts or side products are present and in which there is no danger of colour formation.

The present invention provides such an enzymatic process for preparing sterically hindered esters. It has been found that certain lipases, viz. those having hydrolytic activity with esters in which the alcohol part is sterically hindered around the ester bond enable to prepare such esters from the constituent alcohols and acids.

Therefore, the present invention relates to a process of enzymatically preparing esters of carboxylic acids using a lipase under low-water conditions, which is characterized by the fact, that esters in which the alcohol part is sterically hindered around the ester bond are prepared using a lipase selected from the group consisting of lipase species having hydrolytic activity with the same esters. The lipase which is preferred is *Candida antarctica* lipase A. It is known that *Candida antarctica* lipase contains two constituent lipases A and B, which may be produced from the lipase e.g. by gel filtration. It is also possible to produce them by recombinant DNA technology. The lipase A is more thermostable than the lipase B, but the lipase B has been found not to be able to synthesize the sterically hindered esters according to the present invention. Lipase species having a substrate activity similar to that of *Candida antarctica* lipase A with respect to tertiary alcohol esters can also be used.

The use of mutants and variants of the specific lipases used in the present invention is also considered to be within the scope of the invention. Other lipases which have been found to be suitable in the present invention are the lipases from *Candida rugosa, Geotrichum candidum* and *Candida cylindracae*.

Preferably, the specific lipase to be used according to the present invention is immobilized on an insoluble inorganic or organic carrier by any method which is known per se, e.g. as described in K. Mosbach (editor), Methods in Enzymology, Volume 44, "Immobilized enzymes", Academic Press, New York, 1976.

Particularly preferred are the immobilization methods as described in the European Patent Specifications EP-B-0,232, 933 (AKZO N.V.) and EP-B-0,322,213 and EP-A-0,424,130 (both Unilever NV). In general, these methods comprise the adsorption of the lipase from an aqueous solution onto a hydrophobic particulate, porous solid, selected from hydrophobic polymers, such as olefin homopolymers or copolymers, polystyrene, polyacrylates, polyamides, or hydrophobic inorganic materials, such as silanised silica, glass or ceramic. The solid material is pre-treated with a polar, water-miscible organic solvent in which the solid material is insoluble, but which does not inactivate the lipase, e.g. ethanol.

Suitable materials are for example Accurel EP 100 (Trade Mark, ex AKZO, The Netherlands), and silanised silica Grace 6 1500 MP (Trade Mark, porous silica, ex W. R. Grace, Germany).

In addition lipases can also be immobilized on ion-exchange resins, such as described in European Patent Specification EP-B-140,542 (Novo Nordisk A/S). Lipase is adsorbed from an aqueous solution onto a weak anion-exchange resin, for example Duolite ES-568 (Trade Mark, ex Röhm and Haas, France).

The process may be carried continuously or batch-wise. Preferably, the water of reaction formed is continuously removed by distillation, pervaporation or adsorption on molecular sieves. The temperature at which the reaction can be carried out varies from about 20° C. to about 90° C., preferably from 50° C. to 80° C.

The respective amounts of alcohol and carboxylic acid may vary, but preferably about equimolar amounts are used. The reaction in the process according to the present invention is driven by water removal from the system, such as by co-distillation, addition of desiccants (like molecular sieves), condensation or cold surface technology or pervaporation.

The amount of enzyme used can be up to 30% by weight, based on the total weight of alcohol and acid to be esterified, but preferably from 1% to 20% by weight of enzyme is used.

The process according to the present invention can be effected with no added water, but for those enzymes which require water, the amount of water present (based on the total initial reaction mixture) is at most 5% by weight, preferably at most 2.5% by weight. The acids which can be esterified are saturated or unsaturated, straight or branched chain monocarboxylic acids having from 2 to 54 carbon atoms, such as acetic acid, capric acid, lauric acid, stearic acid, iso-stearic acid, myristic acid, and the unsaturated or poly-unsaturated fatty acids, like oleic acid, linoleic acid and the like. Also polycarboxylic acids like azelaic acid and polymerized acids (as obtained by the polymerization of unsaturated fatty acids having from 8 to 24 carbon atoms) such as trimer acid, dimer acid or hydrogenated dimer acid may be used.

The tertiary alcohols which can be used according to the present invention may have 4 to 54 carbon atoms, such as t-butanol, t-amyl alcohol, Guerbet alcohols, terpene alcohols, and the like. Preferably the side chains do not contain more than 2 carbon atoms. Preferably, the tertiary alcohols are monohydric alcohols.

In the preparation of ester mixtures, various mixtures of monocarboxylic acids may be used.

The invention will now further be illustrated on hand of the following examples.

EXAMPLE I

Oleic acid (purity 90%; 171.55 g) was mixed with tertiary butanol (purity greater than 99%; 45.0 g) together with 4.3 g of distilled water in a vessel with stirring. To this was added 25 g of immobilized *Candida antarctica* lipase A (Code SP433, ex Novo Industri, Denmark) (immobilized on porous polypropylene beads, Accurel EP100, ex Akzo). The temperature of the reaction mixture was raised to 60° C. and this was maintained for 117 hours. Approximately every 24 hours a vacuum was applied to the mixture, typically 20 millibars for one hour, to remove water by codistillation with tertiary butanol. After each vacuum removal a further 45 g of tertiary butanol was added to the reaction mixture.

At the end of the reaction free fatty acid was removed by column purification, using 300 g of alumina (basic activity 2) and 60–80 petroleum ether was used as the eluant. This yielded 66 g of water clear product shown by GC analysis to be tertiary butyl oleate having a conversion of 32% based on oleic acid. The final product contained very little free acid (acid value=0.15).

EXAMPLE II

Oleic acid (purity greater than 99%; 828 mg) was mixed with t-amyl alcohol (purity greater than 99%; 258 mg) together with 23 mg of distilled water. To this was added 62.5 mg of immobilised Candida antarctica liplase A (code SP433, ex Novo Industri, Denmark) as in Example I. The temperature of the reaction mixture was raised to 60° C. After 22 hours the amount of t-amyl oleate formed in the reaction was determined by GC analysis of the sample. 70.4 mg was removed and the mixture eluted down an alumina column (basic activity 2) to remove free fatty acid, using 60–80 petroleum ether as the eluant. 2.5 mg of eicosane was used as an internal standard for GC analysis. A final product yield of 14.8% based on oleic acid was achieved. Confirmation of the product identity was by GCMS.

EXAMPLE III

In the same way as described in Example II linalyl oleate was prepared using 780 mg linalool (purity 97%) and 1427 mg of oleic acid (purity 99%) together with 44 mg of water. To this was added 125 mg of immobilised *Candida antarctica* lipase A (code SP433, ex Novo Industri, Denmark). The temperature of the reaction mixture was raised to 60° C. A final product of 3.0% based on oleic acid was achieved. Confirmation of the product identity was by GCMS.

EXAMPLE IV

In this example a number of immobilised lipases (immobilised on macroporous polypropylene (Accurel, as described in EP-B-322,213) as described in Example I) was investigated as to their suitability to form sterically hindered esters.

Oleic acid (purity greater than 99%; 548 mg) was mixed with tertiary butanol (purity greater than 99%; 144 mg) together with 14 mg of distilled water in a magnetically stirred vessel. To this was added 40 mg of lipase catalyst (see Table 1).

The temperature of the reaction mixture was raised to 40° C. for an extended period of 64 hours.

At the end of the reaction free fatty acid was removed by column purification, using alumina (basic activity 2); 60–80 petroleum ether was used as the eluant.

The amount of t-butyl oleate formed in the reaction was then determined by GC analysis of the sample using 2.5 mg of eicosane as the internal standard.

TABLE 1

| Immobilised lipase | theoretical loading | % product yield |
| --- | --- | --- |
| Control (no lipase) | | 0 |
| *Rhizopus niveus* | 12.5 KLU/G | 0 |
| Arthrobacter | 37.1 KLU/G | 0 |
| *Rhizopus delemar* | 38.4 KLU/G | 0 |
| Humicola | 2.23 KLU/G | 0 |
| *Pseudomonas therm.* | 56.0 KLU/G | 0 |
| Pseudomonas P. | 3.8 KLU/G | 0 |
| *Rhizopus japonicus* | 40.1 KLU/G | 0 |
| Candida rugosa | 10.7 KLU/G | 0.6 |
| Geotrichum candidum | 4.1 KLU/G | 0 |
| Geotrichum candidum | 26.1 KLU/G | 0 |
| Porcine pancreatic lipase | 193.4 KLU/G | 0 |
| Biolipase | 4.83 KLU/G | 0 |
| Cutinase | 22.0 KLU/G | 0 |
| Chromobacter viscosium | 43.7 KLU/G | 0 |
| Pseudomonas glumae | 71.3 KLU/G | 0 |
| Candida antarctica A | 27.0 KLU/G | 5.6 |

From these experiments it was clear that only a few specific lipases could be used in the process according to the present invention.

COMPARATIVE EXAMPLE A

Oleic acid (purity greater than 99%; 858 mg) was mixed with tertiary butanol (purity greater than 99%; 225 mg)

together with 22 mg of distilled water in a magnetically stirred vessel. To this was added 62.5 mg of immobilized lipase catalyst (native *Mucor miehei;* code SP 282, ex Novo Industri A/S, Denmark) and also in a separate run 62.5 mg of immobilised lipase, which was a cloned *Mucor miehei* (code SP 392, ex Novo Industri A/S, Denmark).

The temperature of the reaction mixture was raised to 40° C. and this was maintained for 20 hrs. At the end of the reaction period free fatty acid was removed by column purification using alumina (basic activity 2) with 60–80 petroleum ether used as the eluant. The amount of tertiary butyl oleate formed in the reaction was then determined by GC analysis of the sample using 2.5 mg of eicosane as the internal standard.

TABLE 2

| Immobilized lipase | Code | % Product Yield |
| --- | --- | --- |
| Native *Mucor miehei* | SP282 | 0 |
| Cloned *M. Miehei* | SP392 | 0 |

COMPARATIVE EXAMPLE B

A comparative experiment as described by Zaks and Klibanov (Science 224, p. 1249–51, 1984) was carried out using porcine pancreatic lipase. In addition a comparison was made with *Candida antarctica* A lipase and two further alcoholysis interesterification reactions.

Glycerol tributyrin (purity greater than 9.9%; 0.975 g) was mixed with tertiary-butanol (purity greater than 99%; 0.2392 g) together with 8.5 mg (0.7% by weight) of distilled water. To this was added 125 mg of porcine pancreatic lipase (PPL/EP100 ST623). The temperature of the reaction mixture was raised to 40° C. for a period of 24 hours.

In the same way two further alcoholysis reactions were investigated using porcine pancreatic lipase.

Methyl oleate (purity greater than 99%; 0.859 g) was mixed with tertiary-butanol (purity greater than 99%; 0.2146 g) together with 7.5 mg (0.7% by weight) of distilled water. To this was added 125 mg of the appropriate lipase and incubation at 40° C. for 24 hours.

Similary methyl oleate was mixed with n-butanol in the same way as the previous example as a series of control reactions. Product formation was determined by GC-analysis of the sample. The results have been summarized in Table 3 below.

TABLE 3

| Lipase | Substrates | % product yield |
| --- | --- | --- |
| Porcine pancreatic lipase | t-butanol + tributyrin | 0 |
| Porcine pancreatic lipase | t-butanol + methyl oleate | 0 |
| Porcine pancreatic lipase | n-butanol + methyl oleate | 29.6 |

The experiments clearly show that Zaks and Klibanov's results are negative in the presence of tertiary alcohols.

We claim:

1. A process for the enzymatic preparation of an ester from a carboxylic acid and a tertiary alcohol comprising reacting said carboxylic acid and said tertiary alcohol in the presence of at most 5% by weight of water and a lipase from *Candida antarctica*.

2. A process according to claim 1 wherein the lipase is *Candida antarctica* lipase A.

3. A process according to claim 1 wherein the tertiary alcohol is selected from the group consisting of tertiary alcohols having from 4 to 54 carbon atoms and mixtures thereof.

4. A process according to claim 1 wherein the side chains of the tertiary alcohol do not contain more than 2 carbon atoms.

5. A process according to claim 1 wherein the tertiary alcohol is a tertiary terpene alcohol.

6. A process according to claim 1 wherein the tertiary alcohol is a tertiary monohydric alcohol.

7. A process according to claim 1 wherein the carboxylic acid is selected from the group consisting of monocarboxylic acids having from 2 to 54 carbon atoms, polycarboxylic acids and mixtures thereof.

8. A process according to claim 1 wherein the amount of water present is at most 2.5% by weight, based on the total initial reaction mixture.

9. A process according to claim 1 wherein the lipase is immobilized on an insoluble inorganic or organic carrier.

* * * * *